United States Patent
Lin et al.

(10) Patent No.: US 11,813,181 B2
(45) Date of Patent: Nov. 14, 2023

(54) ABSORBABLE METAL STENT

(71) Applicant: Biotyx Medical (Shenzhen) Co., Ltd., Shenzhen (CN)

(72) Inventors: Wenjiao Lin, Shenzhen (CN); Wenchao Fu, Shenzhen (CN)

(73) Assignee: BIOTYX MEDICAL (SHENZHEN) CO., LTD., Shenzhen (CN)

( * ) Notice: Subject to any disclaimer, the term of this patent is extended or adjusted under 35 U.S.C. 154(b) by 79 days.

(21) Appl. No.: 16/957,941

(22) PCT Filed: Dec. 18, 2018

(86) PCT No.: PCT/CN2018/121737
§ 371 (c)(1),
(2) Date: Jun. 25, 2020

(87) PCT Pub. No.: WO2019/128777
PCT Pub. Date: Jul. 4, 2019

(65) Prior Publication Data
US 2020/0345522 A1 Nov. 5, 2020

(30) Foreign Application Priority Data
Dec. 27, 2017 (CN) .......................... 201711450037.4

(51) Int. Cl.
*A61F 2/915* (2013.01)
*A61L 31/14* (2006.01)
(Continued)

(52) U.S. Cl.
CPC .............. *A61F 2/82* (2013.01); *A61L 31/022* (2013.01); *A61L 31/06* (2013.01); *A61L 31/088* (2013.01);
(Continued)

(58) Field of Classification Search
CPC .............. A61F 2/915; A61F 2210/0004; A61F 2250/003; A61F 2250/0036;
(Continued)

(56) References Cited

U.S. PATENT DOCUMENTS 5,780,807 A * 7/1998 Saunders .................. A61F 2/91 29/557
6,258,117 B1 * 7/2001 Camrud .................... A61F 2/82 623/1.16
(Continued)

FOREIGN PATENT DOCUMENTS

| CN | 1389271 A | 1/2003 |
|----|-----------|--------|
| CN | 1579341 A | 2/2005 |

(Continued)

OTHER PUBLICATIONS

Chinese Office Action dated Jun. 23, 2021, in connection with corresponding CN Application No. 201711450037.4 (22 pp., including machine-generated English translation).
(Continued)

*Primary Examiner* — Brian E Pellegrino
(74) *Attorney, Agent, or Firm* — Maier & Maier, PLLC (57) ABSTRACT

An absorbable metal stent includes an absorbable metal substrate; the absorbable metal substrate includes a plurality of wave-shaped annular structures and a plurality of axial connecting portions, two ends of each axial connecting portion being connected to two adjacent wave-shaped annular structures, respectively, so as to axially connect the plurality of wave-shaped annular structures; a corrosion-promoting coating is formed on each axial connecting portion, the corrosion-promoting coating containing a corrosion-promoting substance, and the corrosion-promoting substance being selected from at least one of a degradable polymer and a degradable polymer antioxidant; the corrosion-promoting coatings cause the corrosion of the axial (Continued)

connecting portions to occur earlier than the corrosion of the plurality of wave-shaped annular structures. The absorbable metal stent has good bending performance and may prevent the problems of secondary hyperplasia after implantation and stenosis caused thereby.

19 Claims, 4 Drawing Sheets

(51) Int. Cl.
- *A61F 2/82* (2013.01)
- *A61L 31/02* (2006.01)
- *A61L 31/06* (2006.01)
- *A61L 31/08* (2006.01)
- *A61L 31/16* (2006.01)

(52) U.S. Cl.
CPC .......... *A61L 31/148* (2013.01); *A61L 31/16* (2013.01); *A61F 2002/91575* (2013.01); *A61F 2210/0004* (2013.01); *A61F 2250/003* (2013.01); *A61F 2250/0067* (2013.01); *A61L 2300/21* (2013.01); *A61L 2300/216* (2013.01); *A61L 2300/40* (2013.01); *A61L 2300/416* (2013.01); *A61L 2420/06* (2013.01)

(58) Field of Classification Search
CPC .... A61F 2210/0076; A61F 2002/91575; A61F 2250/0067; A61F 2/82; A61L 31/148
See application file for complete search history.

(56) References Cited

U.S. PATENT DOCUMENTS

2010/0292776 A1   11/2010  Weber et al.
2013/0236498 A1*  9/2013  Mangiardi ............ A61L 31/148
                                            427/2.24

FOREIGN PATENT DOCUMENTS

| CN | 101513541 A | 8/2009 | |
|---|---|---|---|
| CN | 103705983 A | 4/2014 | |
| CN | 206714858 U | 12/2017 | |
| WO | 03/063733 A1 | 8/2003 | |
| WO | WO-2007059253 A2 * | 5/2007 | ............... A61F 2/82 |
| WO | WO-2008034031 A2 * | 3/2008 | ........... A61L 31/148 |
| WO | WO-2012118696 A1 * | 9/2012 | ............... A61F 2/01 |
| WO | 2017/204803 A1 | 11/2017 | |

OTHER PUBLICATIONS

Extended European Search Report dated Aug. 9, 2021, in connection with corresponding EP Application No. 18894519.0; 7 pages.
Chinese Office Action dated Feb. 2, 2021, in connection with corresponding CN Application No. 201711450037.4 (19 pp., including machine-generated English translation).
Chinese Notification of Registration dated Oct. 20, 2021, in connection with corresponding CN Application No. 201711450037.4 (3 pp., including machine-generated English translation).
International Search Report dated Mar. 14, 2019 in corresponding International Application No. PCT/CN2018/121737; 4 pages.

* cited by examiner

ABSORBABLE METAL STENT

FIELD

The embodiments relate to the field of interventional medical instruments, and more particularly to an absorbable metal stent.

BACKGROUND

Vascular stents can be divided into permanent stents and absorbable stents according to the length of time they remain in blood vessels. The permanent stents are made of non-degradable materials, such as 316L stainless steel, a platinum chromium alloy, a nickel titanium alloy, a cobalt chromium alloy, tantalum, and titanium. These materials exist in the human bodies as foreign bodies for a long time, and thus easily cause excessive intimal hyperplasia, and other problems such as restenosis of the blood vessels in the middle and late stages, chronic inflammations, and late and very late thrombosis. An absorbable stent will gradually degrade after being implanted into the blood vessel and will be absorbed by the body until it completely disappears. It is an ideal choice for the treatment of cardiovascular diseases. The absorbable stent is made of a bioabsorbable material, which may be an absorbable metal-based material such as magnesium-based, iron-based or zinc-based alloy, or an absorbable polymer-based material such as polylactic acid, polycaprolactone, or poly(iodotyrosine alkyl carbonate).

Clinical results have shown that vascular stents have a risk of fracture after implantation. The occurrence of stent fracture is related to material defects and metal fatigue. Metal fatigue refers to the process in which materials and components under cyclic stress or cyclic strain gradually produce local permanent cumulative damage at one or more places, and after a certain number of cycles, cracks or suddenly fractures completely. In the cardiac cycle, an intravascular stent will flex, stretch, and even twist with the movement of blood vessels, as well as the contraction and relaxation of the blood vessels. In tortuous and angled coronary vessels, stent fracture is more likely to occur, so the requirements for the fatigue resistance of metal rods of the stent have also increased. In particular, when the right coronary artery is distorted, with large motion amplitude and obvious lateral motion in the systole, the stent implanted therein withstands higher stress levels and more prone to fracture.

The vascular stent is subject to bending when implanted into curved vessels. In order to improve the bending performance and the compliance with blood vessels of the vascular stent to reduce the stimulation of relative motions between the stent and blood vessels and to avoid the occurrence of vascular injury and dissection, some people use a special design of connecting rods to make at least part of the connecting rods fracture due to an axial force after a period of time after implantation, thereby reducing the axial restraint of the stent, and enhancing bending and compliance performances. However, for a metal stent, stent rods at these fracture locations are in long-term contact with vascular tissues, and hard metal stent rods having strong mechanical properties will continuously stimulate neointimal tissues near the fracture sites for a long time under constant pulsation and/or bending of blood vessels, which will cause secondary hyperplasia and stenosis caused thereby in the middle and late stages after stent implantation.

After the implantation of a normally permanent DES (drug eluting stent), the stenosis rate usually increases slowly with the increase of implantation time, but it will not change much after about one year. The secondary hyperplasia defined in this art generally refers to a case in which the stenosis rate of the vascular area of the stent segment has increased significantly from 30% and below 1 month after implantation to 50% and above within 12 months, which is basically caused by product's abnormalities such as irritation, inflammations or other toxic effects.

For a permanent stent, the fatigue performance of the stent can be improved through methods such as material optimization and stent structure optimization, and can even ensure that the stent is permanently implanted without fatigue fracture, which is a feasible method to reduce or avoid the stimulation of fractured stent rods to neointimal tissues and thus to reduce or avoid the secondary hyperplasia and stenosis caused thereby.

However, for an absorbable stent, material optimization, stent structure optimization and the like can only improve the fatigue performance of the stent without corrosion, and ensure that the stent do not fracture before corrosion begins. For example, it is generally desirable that the stent is not substantially corroded in the early stages of implantation, such as within 3 months or even 6 months, in order to provide adequate mechanical support within 3 months or even 6 months of implantation. In the prior art, a corrosion inhibition layer can be provided on the surface of the absorbable stent to prevent the stent from corroding within a certain period of time (for example, within 3 months or even 6 months). For example, the surface of an iron substrate is coated with a zinc plating layer, an iron phosphate layer, an iron oxide layer, an organic oil layer or the like. However, when corrosion begins, localized areas of the stent will generate gaps or corrosion pits due to the evolution of corrosion, which will easily develop into fatigue crack sources. Under cyclic loading (radial pulsating squeeze action, axial tensile action, bending action, etc.) and continuous corrosion, the crack sources will quickly lose stability and expand, resulting in corrosive fatigue fracture of the stent. In addition, the corrosive fatigue fracture is similar to ordinary fatigue fracture, and has a flush fracture surface, such that no obvious corrosion can be seen generally, and the original shape of the metal rod is also maintained. If the subsequent corrosion of the absorbable metal stent is relatively slow and no obvious corrosion products are formed to wrap the fracture surfaces of the stent rods, the hard metal fractured rods will continue to stimulate the neointimal tissues in the longer period of time under the complex cyclic forces of pulsation, bending and stretching of blood vessels.

Figure 1:
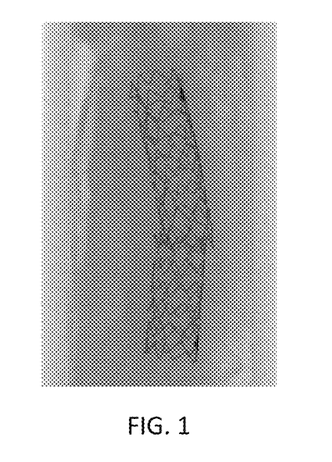
FIG. 1 is a schematic diagram showing a case where an absorbable metal stent of the prior art is fractured by stress.

Meanwhile, the fracture caused by fatigue only occurs in a stress concentration site of the stent, and the entire stent is not deconstructed. The stent parts at both ends of the fracture surface are still a whole. Forces are still transmitted among wave-shaped annular structures. When the stent is fractured, two fractured stent parts may overlap each other in a staggered manner under the force of continuous bending and stretching of the blood vessels. As shown in FIG. 1, the long-term stimulation of the fractured rods at the fractured sites to the neointima is further aggravated. In this case, after 2-3 months of stimulation, intimal hyperplasia may generally occur, which may lead to secondary hyperplasia and stenosis caused thereby in the middle and late stages of stent implantation.

SUMMARY

Based on this, it is necessary to provide an absorbable metal stent, which has better bending performance and can avoid the problem of secondary hyperplasia caused by fractured rods and stenosis caused thereby after implantation.

An absorbable metal stent includes an absorbable metal substrate; the absorbable metal substrate includes a plurality of wave-shaped annular structures and a plurality of axial connecting portions, two ends of each axial connecting portion being connected to two adjacent wave-shaped annular structures respectively so as to axially connect the plurality of wave-shaped annular structures; a corrosion-promoting coating is formed on each of the axial connecting portions, the corrosion-promoting coating containing a corrosion-promoting substance, and the corrosion-promoting substance being selected from at least one of a degradable polymer and a degradable polymer antioxidant; the corrosion-promoting coatings cause the corrosion of the axial connecting portions to occur earlier than the corrosion of the plurality of wave-shaped annular structures.

In one embodiment, the degradable polymer is selected from at least one of a degradable polyester, a degradable polyanhydride, and a degradable polyamino acid; and a chain segment or monomer released when the degradable polymer antioxidant is degraded includes at least one of ascorbic acid, glutathione, lipoic acid, and proanthocyanidin.

In one embodiment, a first corrosion inhibition layer is formed on each of the wave-shaped annular structures. In one embodiment, a second corrosion inhibition layer is formed on each of the axial connecting portions, the corrosion-promoting coating at least partially covers the second corrosion inhibition layer, and the thickness of the first corrosion inhibition layer is greater than or equal to the thickness of the second corrosion inhibition layer.

In one embodiment, each of the wave-shaped annular structures includes a plurality of wave peaks, a plurality of wave troughs, and a plurality of support rods; two ends of each of the support rods are respectively connected to one of the wave peaks and one of the wave troughs, which are adjacent to each other, to form the wave-shaped annular structure; each first corrosion inhibition layer is a coating having a non-uniform thickness, and the thicknesses of portions of the first corrosion inhibition layer located at the wave peak and the wave trough is less than or equal to the thickness of the first corrosion inhibition layer located at the support rod, respectively.

In one embodiment, the absorbable metal substrate is an iron substrate, an iron-based alloy substrate, a magnesium substrate, a magnesium-based alloy substrate, a zinc substrate or a zinc-based alloy substrate. In one embodiment, the wave-shaped annular structures are made of iron or an iron-based alloy, and the axial connecting portions are made of a magnesium alloy.

In one embodiment, the absorbable metal stent further includes a degradable polymer layer provided on each of the wave-shaped annular structures, and the material of the degradable polymer layer is selected from at least one of a degradable polyester, a degradable polyanhydride, and a degradable polyamino acid.

In one embodiment, when the material of the degradable polymer layers is the same as that of the corrosion-promoting coatings, the thickness of each degradable polymer layer is less than or equal to the thickness of each corrosion-promoting coating.

In one embodiment, when the material of the degradable polymer layers and the material of the corrosion-promoting coatings are the same degradable polymer, a molecular weight of the degradable polymer in the corrosion-promoting coatings is less than or equal to a molecular weight of the degradable polymer in the degradable polymer layers.

In one embodiment, when the material of the degradable polymer layers and the material of the corrosion-promoting coatings are the same degradable polymer, a polydispersity coefficient of the degradable polymer in the corrosion-promoting coatings is greater than or equal to a polydispersity coefficient of the degradable polymer in the degradable polymer layers.

In one embodiment, each of the wave-shaped annular structures includes a plurality of wave peaks, a plurality of wave troughs, and a plurality of support rods; two ends of each of the support rods are respectively connected to one of the wave peaks and one of the wave troughs, which are adjacent to each other, to form the wave-shaped annular structure; the degradable polymer layer is a coating having a non-uniform thickness, and the thicknesses of portions of the degradable polymer layer located at the wave peak and the wave trough are greater than or equal to the thickness of the degradable polymer layer located at the support rod, respectively.

In one embodiment, each of the wave-shaped annular structures includes a plurality of wave peaks, a plurality of wave troughs, and a plurality of support rods; two ends of each of the support rods are respectively connected to one of the wave peaks and one of the wave troughs, which are adjacent to each other, to form the wave-shaped annular structure; and a molecular weight of the degradable polymer in portions of the degradable polymer layer located at the wave peak and the wave trough is less than or equal to a molecular weight of the degradable polymer in the degradable polymer layer located at the support rod.

In one embodiment, each of the wave-shaped annular structures includes a plurality of wave peaks, a plurality of wave troughs, and a plurality of support rods; two ends of each of the support rods are respectively connected to one of the wave peaks and one of the wave troughs, which are adjacent to each other, to form the wave-shaped annular structure; and polydispersity coefficients of the degradable polymer in portions of the degradable polymer layer located at the wave peak and the wave trough are greater than or equal to a polydispersity coefficient of the degradable polymer in the degradable polymer layer located at the support rod, respectively.

In one embodiment, the degradable polyester is selected from at least one of polylactic acid, polyglycolic acid, polycaprolactone, polysuccinate, poly($\beta$-hydroxybutyrate), polyethyl dialcohol adipate, and polyhydroxybutyrate valerate; or the degradable polyester is selected from a copolymer formed by copolymerizing at least two kinds of monomers forming polylactic acid, polyglycolic acid, polycaprolactone, polysuccinate, poly($\beta$-hydroxybutyrate), polyethyl dialcohol adipate, and polyhydroxybutyrate valerate.

In one embodiment, the degradable polyanhydride is selected from at least one of polyoxalic anhydride, polybutanedioic anhydride, polyadipic anhydride, polysebacic anhydride, polydodecanoic anhydride, polycitric anhydride, polymalic anhydride, polysuccinic anhydride, polytartaric anhydride, polyitaconic anhydride, and polymaleic anhydride; or the degradable polyanhydride is a copolymer formed by copolymerizing at least one of monomers forming polyoxalic anhydride, polybutanedioic anhydride, polyadipic anhydride, polysebacic anhydride, polydodecanoic anhydride, polycitric anhydride, polymalic anhydride, polysuccinic anhydride, polytartaric anhydride, polyitaconic anhydride and polymaleic anhydride, and at least one of monomers forming polylactic acid, polyglycolic acid, polycaprolactone, polysuccinate, poly(β-hydroxybutyrate), polyethyl dialcohol adipate, and polyhydroxybutyrate valerate.

In one embodiment, the monomer that forms the degradable polyamino acid is selected from at least one of monomers forming polylysine, polyaspartic acid, polycysteine, polymethionine, polyornithine, polyglycine, and polyglutamic acid.

In one embodiment, the corrosion-promoting coatings and/or the degradable polymer layers contain an active drug, the active drug being selected from at least one of a drug that inhibits vascular proliferation, an antiplatelet drug, an antithrombotic drug, an anti-inflammatory drug and an anti-allergenic drug.

In one embodiment, the drug that inhibits vascular proliferation is selected from at least one of paclitaxel, rapamycin and derivatives thereof; the anti-platelet drug is cilostazol; the antithrombotic drug is heparin; the anti-inflammatory drug is dexamethasone; and the anti-allergenic drug is selected from at least one of calcium gluconate, chlorpheniramine and cortisone.

The corrosion-promoting coating is formed on each axial connecting portion of the absorbable metal stent, and contains the corrosion-promoting substance selected from at least one of a degradable polymer and a degradable polymer antioxidant. The corrosion-promoting substance can be degraded to form a local low pH environment or promote the corrosion of the axial connecting portions through antioxidation, and can cause the corrosion of the axial connecting portions to occur earlier than the corrosion of the plurality of wave-shaped annular structures. Corrosive fracture of the plurality of axial connecting portions causes the absorbable metal stent to be axially deconstructed in sequence to form a plurality of independent wave-shaped annular structures, thereby improving the bending performance of the absorbable metal stent.

In addition, the entire absorbable metal stent is deconstructed axially, and the wave-shaped annular structures are no longer connected to each other through the axial connecting portions. Therefore, when the blood vessel bends and pulsates, no force is transferred among the wave-shaped annular structures, thereby greatly reducing the stimulation to neointimal tissues of the blood vessels by the relative motions among the neointimal tissues of the blood vessels.

Meanwhile, the corrosion-promoting substance can significantly promote the corrosion of the absorbable metal stent, so that after the absorbable metal stent is implanted and the corrosive fatigue fracture occurs, the fracture surfaces and the peripheries of the axial connecting portions are quickly corroded. In addition, in a relatively short period of time, a large number of loose and softly-textured corrosion products are formed to wrap the fracture surfaces, thereby preventing the problems of secondary hyperplasia after implantation and stenosis caused thereby due to long-term stimulation of the hard metal fractured rods to neointimal tissues.

DETAILED DESCRIPTION OF THE EMBODIMENTS

In order to make the above objects, features, and advantages of the embodiments more comprehensible, specific embodiments of the embodiments are described in detail below with reference to the accompanying drawings. Numerous details are set forth in the following description to facilitate a full understanding of the embodiments. However, the embodiments can be implemented in many other ways than those described herein, and those of ordinary skill in the art can make similar improvements without departing from the content of the embodiments. Therefore, the embodiments will not be limited by the implementations disclosed below.

Unless defined otherwise, all technical and scientific terms used herein have the same meanings as commonly understood by one of ordinary skill in the art to which the embodiments belongs. The terms used herein in the description of the embodiments are for the purpose of describing particular examples only and are not intended to limit the embodiments.

"Axial" refers to a direction parallel to a connecting line between the center of a distal end and the center of a proximal end of an absorbable metal stent, and "radial" refers to a direction perpendicular to the axial direction.

A coating thickness refers to a vertical distance between the surface of a coating close to a substrate and the surface of the coating away from the substrate.

Figure 2:
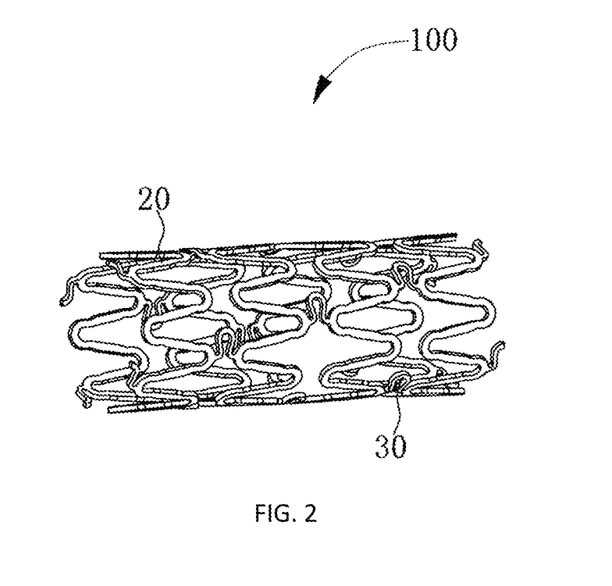
FIG. 2 is a schematic structural diagram of an absorbable metal substrate of an absorbable metal stent according to an embodiment.
Figure 3:
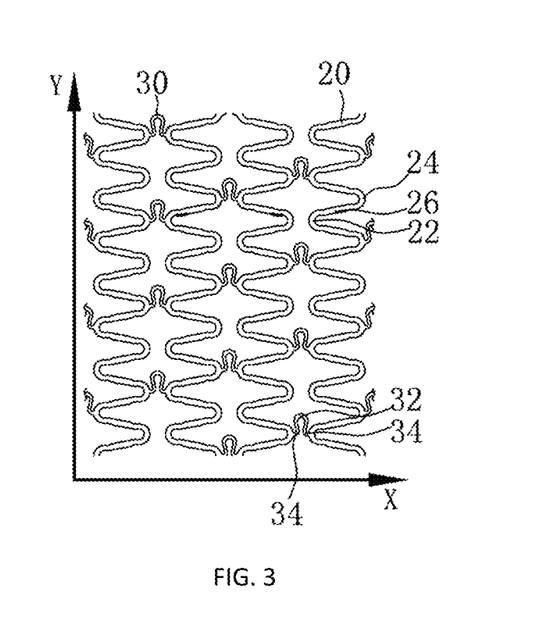
FIG. 3 is a schematic diagram showing axial expansion of FIG. 2.

Referring to FIG. 2, an absorbable metal stent in an embodiment includes an absorbable metal substrate 100. The absorbable metal substrate 100 is a metal substrate capable of being degraded in a living body, such as a pure iron substrate, a nitrided pure iron substrate, an iron-based alloy substrate, a magnesium substrate, a magnesium-based alloy substrate, a zinc substrate or a zinc-based alloy substrate. Referring to FIG. 3 together, the absorbable metal substrate 100 includes a plurality of wave-shaped annular structures 20 and a plurality of axial connecting portions 30.

Each of the wave-shaped annular structures 20 includes a plurality of wave peaks 22, a plurality of wave troughs 24, and a plurality of support rods 26. The wave peaks 22 and the wave troughs 24 are both arc-shaped connecting rods. The support rods 26 are substantially bar-shaped rods. Two ends of each support rod 26 are connected to one wave peak 22 and one wave trough 24, which are adjacent to each other, to form a closed wave-shaped annular structure 20.

Each axial connecting portion 30 is substantially a-shaped, and includes an expandable main body 32 and two connecting portions 34. Each expandable main body 32 is U-shaped or circular with an opening, and the two connecting portions 34 are straight bars or arc-shaped bars. The two connecting portions 34 are respectively provided on two free ends of the expandable main body 32.

The two connecting portions 34 of each axial connecting portion 30 are respectively connected to two adjacent wave-shaped annular structures 20, so that the plurality of wave-shaped annular structures 20 are axially connected to form a hollow lumen structure. In this example, the two connecting portions 34 of each axial connecting portion 30 are respectively connected to two axially opposite wave peaks 22 of two adjacent wave-shaped annular structures 20. Two adjacent wave-shaped annular structures 20 are connected by a plurality of axial connecting portions 30.

Figure 4:
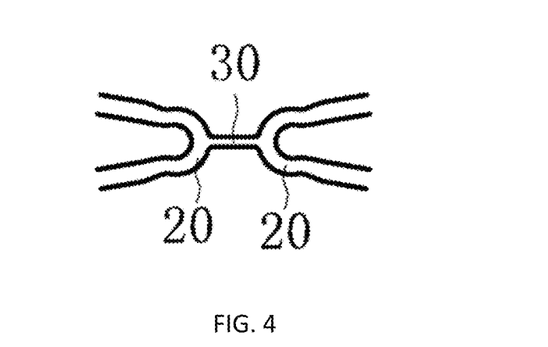
FIG. 4 is a schematic structural diagram of an axial connecting portion according to another embodiment.

When the absorbable metal stent expands, the expandable main bodies 32 of the axial connecting portions 30 having the above-mentioned structures can expand in an axial direction accordingly, and therefore, the length reduction caused by the expansion of the absorbable metal stent can be compensated accordingly. It can be understood that, in other embodiments, the shape of the axial connecting portions 30 is not limited to the above-mentioned Ω shape, and may be other structures. For example, the axial connecting portions 30 may be connecting portions shaped as straight rods (as shown in FIG. 4), S-shaped connecting portions, n-shape connecting portions, dot-shaped connecting portions or the like. Regardless of the shape of the axial connecting portions 30, two free ends of each axial connecting portion 30 are respectively connected to two adjacent wave-shaped annular structures 20.

Figure 5:
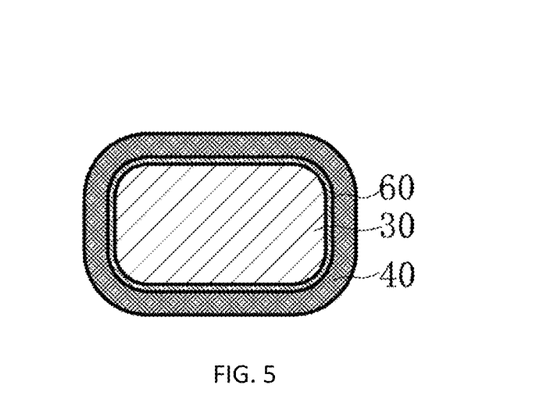
FIG. 5 is a schematic cross-sectional view of an axial connecting portion of the absorbable metal stent shown in FIG. 2.

Referring to FIG. 5, a corrosion-promoting coating 40 is formed on each axial connecting portion 30. In this embodiment, each corrosion-resistant coating 40 covers an outer surface, an inner surface, and side surfaces of each axial connecting portion 30. It may be understood that, in other embodiments, each corrosion-resistant coating 40 may only partially cover the surface of each axial connecting portion 30. For example, each corrosion-resistant coating 40 only covers the outer surface of each axial connecting portion 30.

The corrosion-promoting coatings 40 contain a corrosion-promoting substance. The corrosion-promoting substance is selected from at least one of a degradable polymer and a degradable polymer antioxidant.

The degradable polymer is selected from at least one of a degradable polyester, a degradable polyanhydride, and a degradable polyamino acid. The degradable polyester is selected from at least one of polylactic acid, polyglycolic acid, polycaprolactone, polysuccinate, poly(β-hydroxybutyrate), polyethyl dialcohol adipate, and polyhydroxybutyrate valerate. When the degradable polyester contains two or more components, the two or more components are physically mixed. Alternatively, the degradable polyester is selected from a copolymer formed by copolymerizing at least two kinds of monomers forming polylactic acid, polyglycolic acid, polycaprolactone, polysuccinate, poly(β-hydroxybutyrate), polyethyl dialcohol adipate, and polyhydroxybutyrate valerate.

The degradable polyanhydride is selected from polyoxalic anhydride, polybutanedioic anhydride, polyadipic anhydride, polysebacic anhydride, polydodecanoic anhydride, polycitric anhydride, polymalic anhydride, polysuccinic anhydride, polytartaric anhydride, polyitaconic anhydride, and polymaleic anhydride.

Alternatively, the degradable polyanhydride is a copolymer formed by copolymerizing at least one of monomers forming polyoxalic anhydride, polybutanedioic anhydride, polyadipic anhydride, polysebacic anhydride, polydodecanoic anhydride, polycitric anhydride, polymalic anhydride, polysuccinic anhydride, polytartaric anhydride, polyitaconic anhydride and polymaleic anhydride, and at least one of monomers forming polylactic acid, polyglycolic acid, polycaprolactone, polysuccinate, poly(β-hydroxybutyrate), polyethyl dialcohol adipate, and polyhydroxybutyrate valerate.

The monomer that forms the degradable polyamino acid is selected from at least one of monomers forming polylysine, polyaspartic acid, polycysteine, polymethionine, polyornithine, polyglycine, and polyglutamic acid.

A chain segment or monomer released when the degradable polymer antioxidant is degraded includes at least one of ascorbic acid, glutathione, lipoic acid, and proanthocyanidin.

When the absorbable metal stent is implanted into the body, the degradation of the corrosion-promoting coatings 40 occurs earlier than the corrosion of the absorbable metal substrate 100. The degradation of the corrosion-promoting coatings 40 causes a low pH environment in the tissue environment around the axial connecting portions 30, which can significantly accelerate the corrosion of the axial connecting portions 30. Alternatively, when the material of the axial connecting portions 30 is pure iron or an iron-based alloy, the corrosion-promoting coatings 40 are degraded to release an antioxidant-containing monomer or chain segment, which can prevent $Fe^{2+}$ generated by the corrosion of the axial connecting portions 30 from being oxidized into $Fe^{3+}$ to form a dense ferroferric oxide corrosion product that wraps the surface of the absorbable metal substrate and easily blocks further corrosion of the absorbable metal substrate, but continuously generates a loose, soft and easily dispersed $Fe(OH)_2$ solid corrosion product. Meanwhile, because of a high solubility product, $Fe^{2+}$ is easy to diffuse out and to be absorbed by tissues, so that the corrosion reaction continuously proceeds in the direction of generating $Fe^{2+}$, which greatly promotes the corrosion of the axial connecting portions 30.

By way of stent material optimization, structure optimization and other manners, the fatigue performance of the stent can be ensured, and the fatigue fracture will not occur without corrosion.

After the absorbable metal stent is implanted, when corrosion begins to occur, the corrosion-promoting coatings 40 can accelerate the corrosion of the axial connecting portions 30, making them rapidly corrode after corrosive fatigue fracture. For example, about half a month or about one month, even if the corrosive fatigue fracture of the absorbable metal stent occurs, loose and softly-textured corrosion products will be produced quickly at fracture surfaces to wrap the fracture surfaces, thereby avoiding the problems of secondary hyperplasia and stenosis caused thereby due to long-term stimulation of hard metal rods to the neointimal tissues.

Moreover, the corrosion-promoting coating 40 is formed on each of the axial connecting portions 30, so that the fracture of each of the axial connecting portions 30 occurs before the fracture of the corresponding wave-shaped annular structure 20. Therefore, the absorbable metal stent can be sequentially deconstructed axially to form a plurality of independent wave-shaped annular structures 20. The plurality of independent wave-shaped annular structures 20 can provide support for a lesion in a radial direction. However, since the plurality of wave-shaped annular structures 20 are independent of each other, the absorbable metal stent has better bending performance When the blood vessel bends and pulsates, no force is transferred among the wave-shaped annular structures 20, thereby greatly reducing the stimulation to the neointimal tissues of the blood vessel by the relative motions among the neointimal tissues of the blood vessel.

Therefore, the absorbable metal stent has better bending performance and compliance with blood vessels, and can avoid the problem of secondary hyperplasia and stenosis caused thereby after implantation.

Figure 6:
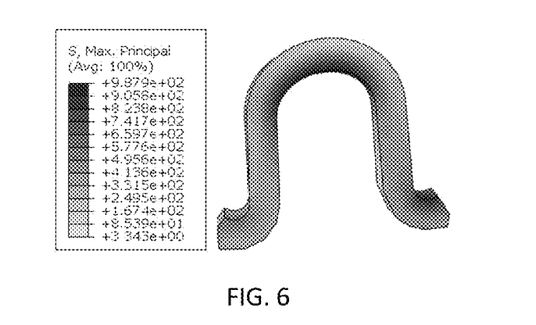
FIG. 6 is a deformation stress cloud diagram of the axial connecting portion of the absorbable metal stent shown in FIG. 1.

For example, each corrosion-promoting coating 40 is a coating having a non-uniform thickness. The thickness of a stress concentration area on the corrosion-promoting coating layer 40 on each axial connecting portion 30 is greater than the thickness of other regions. Referring to FIG. 6, for each axial connecting portion 30 in this embodiment, the top of the expandable main body 32, that is, a position of the expandable main body 32 over against the open end is the stress concentration area. Therefore, the thickness of a portion of the corrosion-resistant coating 40 on the top of the expandable main body 32 is relatively large.

Figure 7:
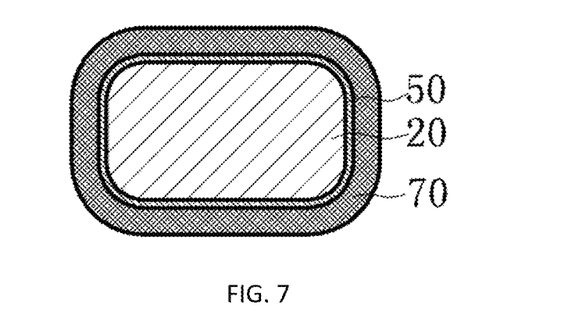
FIG. 7 is a schematic cross-sectional view of a wave-shaped annular structure of the absorbable metal stent shown in FIG. 2.

Referring to FIG. 7, a first corrosion inhibition layer 50 is formed on each of the wave-shaped annular structures 20. The material of each first corrosion inhibition layer 50 is a bioabsorbable material, and can cause the first corrosion inhibition layer 50 to degrade or dissolve to generate degradation or dissolution products that cover the surface of the wave-shaped annular structure 20, thereby delaying the corrosion of the wave-shaped annular structure 20. For example, when the absorbable metal substrate 100 is an iron substrate, that is, when the material of the wave-shaped annular structures 20 is pure iron, the material of the first corrosion inhibition layers 50 may be zinc. Zinc may be a zinc elementary substance and/or a zinc alloy, or may be a zinc compound, such as zinc phosphate, zinc lactate, or zinc gluconate. For another example, the material of the first corrosion inhibition layers 50 may be sodium silicate. Zinc corrosion products generated by the corrosion of the first corrosion inhibition layers 50 can cover the surfaces of the wave-shaped annular structures 20 to protect the wave-shaped annular structures 20, such that the wave-shaped annular structures 20 maintain a relatively complete structure when the axial connecting portions 30 are corroded and fractured, thereby providing effective radial support for a lesion site for a sufficient time (generally ≥3 months). In this embodiment, each first corrosion inhibition layer 50 covers all surfaces of the corresponding wave-shaped annular structure 20. It can be understood that, in other embodiments, each first corrosion inhibition layer 50 may cover only a part of the surfaces of the corresponding wave-shaped annular structure 20, for example, only the outer surface of the wave-shaped annular structure 20.

Each first corrosion inhibition layer 50 may be a coating having a uniform thickness or a coating having a non-uniform thickness. When each first corrosion inhibition layer 50 is a coating having a non-uniform thickness, the thicknesses of portions of the first corrosion inhibition layer 50 located at the wave peak 22 and the wave troughs 24 are less than or equal to the thickness of the first corrosion inhibition layer 50 located at the support rod 26 respectively, thereby facilitating the corrosive fracture of the wave-shaped annular structures 20 starting at the wave peaks 22 and/or the wave troughs 24.

Referring to FIG. 5 again, a second corrosion inhibition layer 60 is formed on each of the wave-shaped annular structures 30. The material of each second corrosion inhibition layer 60 is a bioabsorbable material, and can cause the second corrosion inhibition layer 60 to degrade or dissolve to generate degradation products that cover the surface of the corresponding axial connecting portion 30, thereby delaying the corrosion of the axial connecting portion 30. For example, when the absorbable metal substrate 100 is an iron substrate, that is, when the material of the axial connecting portions 30 is pure iron, the material of the second corrosion inhibition layers 60 may be zinc. Zinc may be a zinc elementary substance and/or a zinc alloy, or a zinc compound, such as zinc phosphate, zinc lactate or zinc gluconate. The zinc corrosion products generated by the corrosion of the second corrosion inhibition layers 60 can cover the surfaces of the axial connecting portions 30 to protect the axial connecting portions 30. For another example, the material of the second corrosion inhibition layers 60 may be sodium silicate. In this embodiment, each second corrosion inhibition layer 60 completely covers the surface of the corresponding axial connecting portion 30, that is, covers an outer surface, an inner surface and side surfaces of the axial connecting portion 30.

Each corrosion-promoting coating layer 40 completely covers the surface of the corresponding second corrosion inhibition layer 60. By providing the corrosion-promoting coating layer 40 and the second corrosion inhibition layer 60 on each axial connecting portion 30 at the same time, the axial connecting portion 30 can be protected from premature corrosive fracture, such that the complete structure of the absorbable metal stent can be maintained at an early stage to keep the stent intact. It may be understood that, in other embodiments, each corrosion-promoting coating 40 may only partially cover the corresponding second corrosion inhibition layer 60.

Further, in an example, the thickness of each first corrosion inhibition layer 50 is greater than or equal to the thickness of each second corrosion inhibition layer 60, so as to control that the time for the complete degradation of the first corrosion inhibition layer 50 is later than or equal to the second corrosion inhibition layer 60. When the thickness of each first corrosion inhibition layer 50 is the same as the thickness of each second corrosion inhibition layer 60, the first corrosion inhibition layers 50 and the second corrosion inhibition layers 60 can respectively protect the wave-shaped annular structures 20 and the axial connecting portions 30 to control the premature corrosion of the wave-shaped annular structures 20 and the axial connecting portions 30, respectively. Furthermore, due to the corrosion-promoting effect of the corrosion-promoting coatings 40, the corrosive fracture of the axial connecting portions 30 take precedence over the corrosive fracture of the wave-shaped annular structures 20. When the thickness of each first corrosion inhibition layer 50 is greater than the thickness of each second corrosion inhibition layer 60, the protection effects of the first corrosion inhibition layers 50 and the second corrosion inhibition layers 60 are different, thereby further ensuring that the corrosive fracture of the axial connecting portions 30 takes precedence over the corrosive fracture of the wave-shaped annular structures 20.

In a further embodiment, corrosion rates or degradation rates of the first corrosion inhibition layers 50 and the second corrosion inhibition layers 60 may be formed by using materials with different corrosion rates or different degradation rates, respectively, thereby further controlling the wave-shaped annular structures 20 and the axial connecting portions 30 from to be corroded and fractured at different times after implantation. For example, when the wave-shaped annular structures 20 and the axial connecting portions 30 are both formed of pure iron, the material of the first corrosion inhibition layers 50 is zinc, and the material of the second corrosion inhibition layers 60 is magnesium. The corrosion rate of magnesium is greater than that of zinc. Therefore, after implantation, the second corrosion inhibition layers 60 will corrode earlier than the first corrosion inhibition layers 50, thereby ensuring that the corrosive fracture of the axial connecting portions 30 occurs earlier than the corrosive fracture of the wave-shaped annular structures 20.

In view of absorbable metal stents with different substrate materials and wall thickness and different coating materials, the thicknesses of the first corrosion inhibition layers 50 and the second corrosion inhibition layers 60 can be adjusted to protect the absorbable metal substrate 100 during the repair period of the lesion. For example, for a vascular stent of which an absorbable metal substrate 100 is a nitrided pure iron substrate and which has a wall thickness of 50-70 μm, the thickness of the first corrosion inhibition layers and the thickness of the second corrosion inhibition layer 60 are, for example, 0.4-2 μm, respectively. Referring to FIG. 7 again, in an embodiment, a degradable polymer layer 70 is formed on each of the wave-shaped annular structures 20. Each degradable polymer layer 70 at least partially covers the surface of the first corrosion inhibition layer 50. In this embodiment, each degradable polymer layer 70 completely covers the surface of the first corrosion inhibition layer 50. When the degradable polymer layers 70 are degraded, a local low pH environment is generated around the wave-shaped annular structures 20, thereby facilitating the degradation of the wave-shaped annular structures 20.

The material of the degradable polymer layers 70 is selected from at least one of a degradable polyester, a degradable polyanhydride, and a degradable polyamino acid.

The degradable polyester is selected from at least one of polylactic acid, polyglycolic acid, polycaprolactone, polysuccinate, poly(β-hydroxybutyrate), polyethyl dialcohol adipate, and polyhydroxybutyrate valerate. When the degradable polyester contains two or more components, the two or two components are physically mixed. Alternatively, the degradable polyester is selected from a copolymer formed by copolymerizing at least two kinds of monomers forming polylactic acid, polyglycolic acid, polycaprolactone, polysuccinate, poly(β-hydroxybutyrate), polyethyl dialcohol adipate, and polyhydroxybutyrate valerate.

The degradable polyanhydride is selected from at least one of polyoxalic anhydride, polybutanedioic anhydride, polyadipic anhydride, polysebacic anhydride, polydodecanoic anhydride, polycitric anhydride, polymalic anhydride, polysuccinic anhydride, polytartaric anhydride, polyitaconic anhydride, and polymaleic anhydride.

Alternatively, the degradable polyanhydride is a copolymer formed by copolymerizing at least one of monomers forming polyoxalic anhydride, polybutanedioic anhydride, polyadipic anhydride, polysebacic anhydride, polydodecanoic anhydride, polycitric anhydride, polymalic anhydride, polysuccinic anhydride, polytartaric anhydride, polyitaconic anhydride and polymaleic anhydride, and at least one of monomers forming polylactic acid, polyglycolic acid, polycaprolactone, polysuccinate, poly(β-hydroxybutyrate), polyethyl dialcohol adipate, and polyhydroxybutyrate valerate.

The monomer that forms the degradable polyamino acid is selected from at least one of monomers forming polylysine, polyaspartic acid, polycysteine, polymethionine, polyornithine, polyglycine, and polyglutamic acid.

The molecular weights of the degradable polymer in portions of each degradable polymer layer 70 located at the wave peak 22 and the wave trough 24 of the wave-shaped annular structure 20 are less than or equal to the molecular weight of the degradable polymer in a portion of the degradable polymer layer 70 located at the support rod 26. The molecular weights of the degradable polymer in portions of each degradable polymer layer 70 located at the wave peak 22 and the wave trough 24 of the wave-shaped annular structure 20 are less than the molecular weight of the degradable polymer in a portion of the wave-shaped annular structure 20 located at the support rod 26, such that a degradation rate of the portions of the degradable polymer layer 70 located at the wave peak 22 and the wave trough 24 of the wave-shaped annular structure 20 is relatively large, thereby facilitating the corrosive fracture at the wave peak 22 and the peak trough 24 to occur no later than the corrosive fatigue fracture of the support rod 26.

Polydispersity coefficients of the degradable polymer in portions of each degradable polymer layer 70 located at the wave peak 22 and the wave trough 24 of the wave-shaped annular structure 20 are greater than or equal to a polydispersity coefficient of the degradable polymer in a portion of the degradable polymer layer 70 located at the support rod 26 of the wave-shaped annular structure 20.

When the polydispersity coefficients of the degradable polymer in portions of the wave peak 22 and the wave trough 24 are equal to the polydispersity coefficient of the degradable polymer in a portion of the support rod 26, the corrosive fatigue fracture at the wave peak and the peak trough is controlled to occur earlier than the corrosive fatigue fracture of the support rod 26, by enabling the thicknesses of the portions of the degradable polymer layer 70 located at the wave peak 22 and the wave trough 24 of the wave-shaped annular structure 20 to be respectively greater than the thickness of the degradable polymer layer 70 located at the support rod 26, and/or enabling the molecular weight of the degradable polymer in portions of the degradable polymer layer 70 located at the wave peak 22 and the wave trough 24 of the wave-shaped annular structure 20 to be less than the molecular weight of the degradable polymer in a portion of the degradable polymer layer 70 located at the support rod 26 of the wave-shaped annular structure 20. When the polydispersity coefficients of the degradable polymer in portions of the degradable polymer layer 70 located at the wave peak 22 and the wave trough 24 of the wave-shaped annular structure 20 are greater than the polydispersity coefficient of the degradable polymer in a portion of the degradable polymer layer 70 located at the support rod 26 of the wave-shaped annular structure 20, it can be further ensured that the corrosive fatigue fracture at the wave peaks and/or wave troughs occurs earlier than the corrosive fatigue fracture of the support rods 26.

When the corrosion-promoting substance in the corrosion-promoting coating layers 40 is a degradable polymer, the materials of the corrosion-promoting coatings 40 and the degradable polymer layers 70 may be the same or different.

When the materials of the corrosion-promoting coatings 40 and the degradable polymer layers 70 are the same, and the wave-shaped annular structures 20 and the axial connecting portions 30 are formed of the same material, the thickness of the degradable polymer layers 70 is less than or equal to the thickness of the corrosion-promoting coatings 40. The thicker the polymer layers, the thicker the degradable polymer layers 70 wrapping the absorbable metal substrate 100, the greater the amount of polymer, the less the pH value of the local low-pH environment, and the more favorable for the corrosion of the wave-shaped annular structures 20 or the axial connecting portions 30. The thickness of each degradable polymer layer 70 is less than or equal to the thickness of each corrosion-promoting coating 40. When the thickness of each degradable polymer layer 70 is equal to the thickness of each corrosion-promoting coating 40, the thickness of the first corrosion inhibition layer 50 is set to be greater than the thickness of the second corrosion inhibition layer 60, thereby ensuring that the corrosive fracture of the wave-shaped annular structures 20 occurs later than the corrosive fracture of the axial connecting portions 30. The thickness of each degradable polymer layer 70 is set to be greater than the thickness of the corrosion-promoting coating 40, thereby ensuring that the corrosive fracture of the wave-shaped annular structures 20 occurs later than the corrosive fracture of the axial connecting portions 30.

In view of absorbable metal stents with different substrate materials and wall thickness and different coating materials, the coating thickness can be adjusted to achieve rapid corrosion of the absorbable metal stent at the right time. For example, in view of a vascular stent of which an absorbable metal substrate 100 is a nitrided pure iron substrate and which has a wall thickness of 50-70 μm, when the corrosion-promoting substance of the corrosion-promoting coatings 40 is a degradable polymer, if the corrosion-promoting coatings 40 are too thick, premature deconstruction of the absorbable metal stent will be caused. Moreover, when the corrosion-promoting coatings 40 are too thick, the cross-sectional dimension of the absorbable metal stent will be affected, which makes the absorbable metal stent poor in bending performance and not conducive to transporting and traversing the lesion, and affects the wall adherence performance of the stent, thereby greatly interfering with blood flow and possibly causing thrombosis and other risks. However, if the corrosion-promoting coatings 40 are too thin, they will be quickly degraded and be absorbed by the human body and disappear, and thus cannot play the role of accelerated corrosion in the later stage. Therefore, in the embodiment, the thickness of each corrosion-promoting coating 40 is 6-25 μm, and the thickness of each degradable polymer layer 70 is 5-16 μm.

When the material of the corrosion-promoting coatings 40 is the same as the material of the degradable polymer layers 70, in a yet further embodiment, a molecular weight of the degradable polymer in the corrosion-promoting coatings 40 is less than or equal to a molecular weight of the degradable polymer in the degradable polymer layers 70. The larger the molecular weight, the tighter the structure of the degradable polymer and the slower the degradation rate. When the molecular weight of the degradable polymer in the corrosion-promoting coatings 40 is equal to the molecular weight of the degradable polymer in the degradable polymer layers 70, by reasonably adjusting the thicknesses of the first corrosion inhibition layers 50 and the second corrosion inhibition layers 60, the corrosive fracture of the wave-shaped annular structures 20 occurs later than the corrosive fracture of the axial connecting portions 30. When the molecular weight of the degradable polymer in the corrosion-promoting coatings 40 is greater than the molecular weight of the degradable polymer in the degradable polymer layers 70, the degradation rate of the degradable polymer layers 70 is less than the degradation rate of the corrosion-promoting coatings 40, which further ensures that the corrosive fracture of the wave-shaped annular structures 20 occurs later than the corrosive fracture of the axial connecting portions 30.

When the material of the corrosion-promoting coatings 40 is the same as the material of the degradable polymer layers 70, in a yet further embodiment, the polydispersity coefficient of the degradable polymer in the corrosion-promoting coatings 40 is greater than or equal to the molecular weight of the degradable polymer in the degradable polymer layers 70. The larger the polydispersity coefficient of the degradable polymer, the wider the molecular weight distribution of the polymer, and therefore the more polymers with less molecules, the faster the degradation rate. When the polydispersity coefficient of the degradable polymer in the corrosion-promoting coatings 40 is equal to the polydispersity coefficient of the degradable polymer in the degradable polymer layers 70, the corrosive fracture of the wave-shaped annular structures 20 occurs later than the corrosive fracture of the axial connecting portions 30, by reasonably adjusting the thicknesses of the corrosion-promoting coating layers 40 and the degradable polymer layers 70 and/or reasonably adjusting the thicknesses of the first corrosion inhibition layers 50 and the second corrosion inhibition layers 60. When the polydispersity coefficient of the degradable polymer in the corrosion-promoting coatings 40 is greater than the polydispersity coefficient of the degradable polymer in the degradable polymer layers 70, the degradation rate of the corrosion-promoting coatings 40 is greater than the degradation rate of the degradable polymer layers 70, which further ensures that the corrosive fracture of the wave-shaped annular structures 20 occurs later than the corrosive fracture of the axial connecting portions 30.

It can be understood that when the material of the corrosion-promoting coatings 40 is the same as the material of the degradable polymer layers 70, the thickness of each degradable polymer layer 70 is made less than the thickness of each corrosion-promoting coating 40, and the molecular weight of the degradable polymer in the corrosion-promoting coatings 40 is less than the molecular weight of the degradable polymer in the degradable polymer layers 70. In addition, the polydispersity coefficient of the degradable polymer in the corrosion-promoting coatings 40 is greater than the polydispersity coefficient of the degradable polymer in the degradable polymer layers 70, such that there is a large time difference between the corrosive fracture of the wave-shaped annular structures 20 and the corrosive feature of the axial connecting portions 30, and the axial connection begins to corrode earlier than the wave-shaped annular structures.

When the materials of the corrosion-promoting coatings 40 and the degradable polymer layers 70 are different, the degradation rate of the degradable polymer in the corrosion-promoting coatings 40 is greater than the degradation rate of the degradable polymer in the degradable polymer layers 70, which further ensures that the corrosive fracture of the wave-shaped annular structures 20 occurs later than the corrosive fracture of the axial connecting portions 30.

For example, when the corrosion-promoting substance in the corrosion-promoting coatings 40 is a degradable polymer, the degradable polymer in the corrosion-promoting coatings 40 has a molecular weight of 50,000 to 500,000, and a polydispersity coefficient of 1.2-10; and the degradable polymer in the degradable polymer layers has a molecular weight of 100,000 to 1,000,000, and a polydispersity coefficient of 1.1-10.

According to the above-mentioned absorbable metal stent, the corrosion-promoting coatings 40 are provided on the axial connecting portions 30 to control the speeds of the corrosive fracture of the axial connecting portions 30 and the wave-shaped annular structures 20 to be different, such that the corrosive fracture of the axial connecting portions 30 occur earlier than the corrosive fracture of the wave-shaped annular structures 20 to achieve the orderly axial deconstruction of the absorbable metal stent, thereby improving the bending performance. Under the action of the corrosion-promoting coatings 40, after the corrosive fatigue fracture of the absorbable metal stent occurs, a large number of loose and softly-textured corrosion products are formed at the fracture positions to wrap the fracture surfaces, thereby preventing long-term stimulation of the hard metal fractured rods to neointimal tissues. Therefore, the absorbable metal stent has better bending performance and can avoid the problem of secondary hyperplasia due to fractured rods after implantation and stenosis thereby.

In another embodiment, the material of the wave-shaped annular structures 20 is different from the material of the axial connecting portions 30, and the corrosion rate of the material of the wave-shaped annular structures 20 is less than that of the material of the axial connecting portions 30, thereby further ensuring that the corrosive fracture of the axial connecting portions 30 occurs earlier than the corrosive fracture of the wave-shaped annular structures 20.

It can be understood that the first corrosion inhibition layers 50, the second corrosion inhibition layers 60, and the degradable polymer layers 70 may be omitted. The reasonable provision of the corrosion-promoting coatings 40 only on the axial connecting portions 30 can obtain the effects of making the absorbable metal stent have better bending performance and avoiding the problem of secondary hyperplasia due to broken rods after implantation and stenosis caused thereby.

However, the first corrosion inhibition layers 50 are provided on the basis of the corrosion-promoting coatings 40, which can further ensure that the wave-shaped annular structures 20 remain relatively intact to provide necessary radial support when the axial connecting portions 30 are corroded and fractured. On this basis, the second corrosion inhibition layers 60 are further provided, so that the second corrosion inhibition layers 60 and the corrosion-promoting coatings 40 cooperate with each other, which can further control the corrosive fracture time of the axial connecting portions 30 and prevent the axial connecting portions 30 from too early corrosion. Furthermore, the absorbable metal stent is provided with corrosion-promoting coatings 40, degradable polymer layers 70, first corrosion inhibition layers 50, and second corrosion inhibition layers 60 thereon. The first corrosion inhibition layers 50 protect the wave-shaped annular structures 20 from corrosion within a specific time (for example, 3 months) after implantation. The degradable polymer layers 70 are used to accelerate the corrosion of the wave-shaped annular structures 20 after being implanted for a certain period of time, so as to reduce adverse reactions caused by long-term retention of a metal instrument in the human body. The corrosion-promoting coatings 40 and the second corrosion inhibition layers 60 cooperate with each other, which can further control the corrosion fracture time of the axial connecting portions 30 and prevent the axial connecting portions 30 from too early corrosion.

It can be noted that when each wave-shaped annular structure 20 is provided with the first corrosion inhibition layer 50 and the degradable polymer layer 70 and each axial connecting portion 30 is provided with the corrosion-promoting coating 40 and the second corrosion inhibition layer 60, and when the material of the first corrosion inhibition layers 50 is the same as the material of the second corrosion inhibition layers 60 are the same, the material of the corrosion-promoting coating layers 40 is also the same as the material of the degradable polymer layers 70, the corrosion of the axial connecting portions 30 can occur earlier than the corrosion of the wave-shaped annular structures 20 as long as at least one of the following conditions is satisfied:

1. the thickness of the first corrosion inhibition layers 50 is greater than the thickness of the second corrosion inhibition layers 60;

2. the thickness of the corrosion-promoting coatings 40 is greater than the thickness of the degradable polymer layers 70;

3. the molecular weight of the degradable polymer in the corrosion-promoting coatings 40 is less than the molecular weight of the degradable polymer in the degradable polymer layers 70; and 4. the polydispersity coefficient of the degradable polymer in the corrosion-promoting coatings 40 is greater than the polydispersity coefficient of the degradable polymer in the degradable polymer layers 70.

It can be noted that when each wave-shaped annular structure 20 is provided with the first corrosion inhibition layer 50 and the degradable polymer layer 70 thereon and each axial connecting portion 30 is provided with the corrosion-promoting coating 40 and the second corrosion inhibition layer 60 thereon, and when the material of the first corrosion inhibition layers 50 is the same as the material of the second corrosion inhibition layers 60, the material of the corrosion-promoting coatings 40 is also the same as the material of the degradable polymer layers 70, the above four conditions can be satisfied at the same time, which can further ensure that the corrosion of the axial connecting portions 30 occurs earlier than that of the wave-shaped annular structures 20.

For example, the thicknesses of portions of the degradable polymer layer 70 located at the wave peak 22 and the wave trough 24 on each of the wave-shaped annular structures 20 are greater than or equal to the thickness of the degradable polymer layer 70 located on the support rod 26, respectively. When the thicknesses of portions of the degradable polymer layer 70 located at the wave peak 22 and the wave trough 24 on each of the wave-shaped annular structures 20 is greater than the thickness of the degradable polymer layer 70 located on the support rod 26, the thickness of the portion of the degradable polymer layer 70 located at the wave peak 22 on each of the wave-shaped annular structures 20 and the thickness of the portion located at the peak trough 24 may be equal or different.

Figure 8:
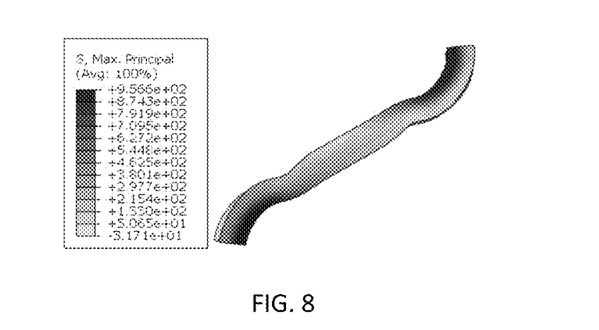
FIG. 8 is a deformation stress cloud diagram of the wave-shaped annular structure of the absorbable metal stent shown in FIG. 1.

The corrosion-promoting coatings 40 and the degradable polymer layers 70 are provided in the above-mentioned two ways, so that the corrosive fracture of the wave-shaped annular structures 20 themselves, that is, the radial deconstruction starts from the corrosive fracture of portions at the wave peaks 22 or the wave troughs 24. Referring to FIG. 8, the wave peaks 22 and the wave troughs 24 are stress concentration regions. Compared with the support rods 26, the wave peaks 22 and the wave troughs 24 are more prone to corrosive fatigue fracture. In order to avoid corrosive fatigue fracture and the production of hard metal rods, the thicknesses of the degradable polymer layers 70 at different locations on the wave-shaped annular structures 20 can be set reasonably, and the wave-shaped annular structures 20 can be controlled to be radially deconstructed in order, thereby further avoiding the problem secondary hyperplasia caused by long-term stimulation of the hard metal rods to the neointimal tissues and stenosis caused thereby, and improving the clinical application safety of the absorbable metal stent.

For example, both the corrosion-promoting coatings 40 and the degradable polymer layers 70 contain an active drug. The active drug is selected from at least one of a drug that inhibits vascular proliferation, an antiplatelet drug, an antithrombotic drug, an anti-inflammatory drug and an anti-allergenic drug. Further, the drug that inhibits angiogenesis is selected from at least one of paclitaxel, rapamycin, and a rapamycin derivative. The antiplatelet drug is cilostazol. The antithrombotic drug is heparin. The anti-inflammatory drug is dexamethasone. The anti-allergenic drug is selected from at least one of calcium gluconate, chlorpheniramine and cortisone.

It can be understood that, in other embodiments, the drug may be carried only in the corrosion-promoting coatings 40 or the drug may be carried only in the degradable polymer layers 70, as long as the amount of the drug carried satisfies the requirements.

It can be understood that the preparation of the absorbable metal stent can be prepared by methods known to those of ordinary skill in the art. For example, laser cutting is used to cut a metal pipe. The plurality of wave-shaped annular structures 20 capable of absorbing the metal substrate 100 and the plurality of axial connecting portions 30 are of an integrated structure. Then, the first corrosion inhibition layers 50, the second corrosion inhibition layers 60, the corrosion-promoting coatings 40 and the degradable polymer layers 70 are correspondingly formed on the absorbable metal substrate 100 by a coating method such as ultrasonic atomization spraying, spin coating, electroplating, or electrostatic spinning. Alternatively, after a plurality of wave-shaped annular structures 20 and a plurality of axial connecting portions 30 are processed and prepared respectively, two ends of each of the plurality of axial connecting portions 30 are connected to two adjacent wave-shaped annular structures 20 to form the absorbable metal substrate 100 of a lumen structure by welding, riveting, hinge connection, inlaying, or the like. Then, the first corrosion inhibition layers 50, the second corrosion inhibition layers 60, the corrosion-promoting coatings 40 and the degradable polymer layers 70 are correspondingly formed on the absorbable metal substrate 100 by a coating method such as ultrasonic atomization spraying, spin coating, electroplating, or electrostatic spinning.

The above-mentioned absorbable metal stent is further explained in the following through specific examples.

The following test methods are used in the following examples:

1. Test method for coating thickness:

the coating thickness test in the examples is performed on a Q-SIX cardiovascular stent tester produced by SENFOFAR company. This tester can test the thickness of a coating by using a light interference principle without damaging the coating.

2. Observation method of a state of the absorbable metal stent in an animal:

the stent corrosion is mainly observed at different time points, such as in the first, third, sixth or twelfth month after the stent is implanted in the animal After the animal is euthanized, the stent and the tissues in its location are removed from the body. The stent corrosion is observed by placing the stent together with the vessel segment where the stent is located under Micro-CT. The stenosis of the stent after implantation in the animal is measured by optical coherence tomography (OCT).

3. Determination method of weight average molecular weight and polydispersity coefficient of a polymer:

the weight-average molecular weight of the polymer is measured using a GPC-multi-angle laser light scattering instrument combined with a molecular weight test system from Wyatt Company in US. This test system includes a liquid pump and a sampler from Agilent in US, an Agilent PL MIXED-C GPC column (size: 7.5×300 mm, 5 μm) from Agilent in US, and a multi-angle laser light scattering instrument and a differential detector from Wyatt in US. The detection conditions are as follows: mobile phase: tetrahydrofuran; pump flow rate: 1 mL/min; injection volume: 100 μL; laser wavelength: 663.9 nm; test temperature: 35° C.

EXAMPLE 1

An absorbable metal stent is an absorbable coronary stent, which includes an absorbable metal substrate. The material of the absorbable metal substrate is nitrided iron. The stent has a wall thickness of 53 μm. The absorbable metal substrate includes eight wave-shaped annular structures which are connected through axial connecting portions and axially arranged, where every two adjacent wave-shaped annular structures are connected by four axial connecting portions. Each wave-shaped annular structure includes 8 wave peaks, 8 wave troughs and 16 support rods. Each axial connecting portion is an Ω connecting portion, and two free ends of each Ω connecting portion are respectively connected to two adjacent wave-shaped annular structures. A first corrosion inhibition layer is provided on each of the wave-shaped annular structures to cover an outer surface, an inner surface and side surfaces of the wave-shaped annular structure. The material of the first corrosion inhibition layers is zinc. Each first corrosion inhibition layer has a thickness of 0.8 μm. A second corrosion inhibition layer is provided on each axial connecting portion to cover an outer surface, an inner surface and side surfaces of the axial connecting portion. The material of the second corrosion inhibition layers is zinc. Each second corrosion inhibition layer has a thickness of 0.8 μm. A corrosion-promoting coating is further provided on each axial connecting portion to cover the surface of the second corrosion inhibition layer, and the material of the corrosion-promoting coatings is polylactic acid. A degradable polymer layer is also provided on each wave-shaped annular structure to cover the surface of the first corrosion inhibition layer, and the material of the degradable polymer layers is also polylactic acid. Both the corrosion-promoting coatings and the degradable polymer layers contain rapamycin. Each corrosion-promoting coating has a thickness of 20 μm, a molecular weight of 200,000, and a polydispersity coefficient of 1.35. Each degradable polymer layer has a thickness of 12 μm, a molecular weight of 200,000, and a polydispersity coefficient of 1.35.

Figure 9:
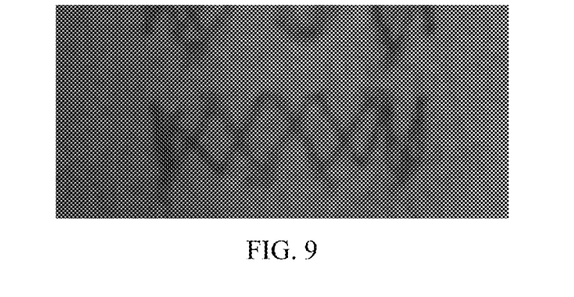
FIG. 9 is a Micro-CT picture of an absorbable coronary stent in Example 1 after 4 months of implantation.
Figure 10:
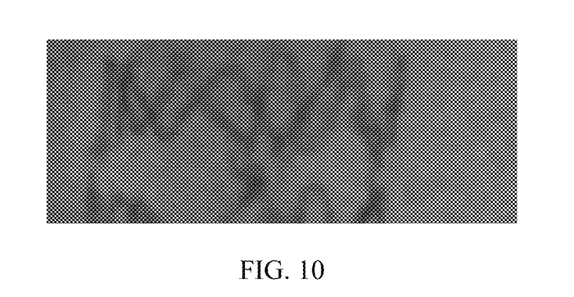
FIG. 10 is a Micro-CT picture of the absorbable coronary stent in Example 1 after 6 months of implantation.

The absorbable coronary stent is implanted into the coronary artery of a pig, and the over-expansion ratio is maintained during the implantation process from 1.1:1 to 1.2:1. The absorbable coronary stent is kept intact in the third month. In the fourth month, the axial connecting portions fracture in the fourth month, and the absorbable coronary stent is axially deconstructed. As can be seen from FIG. 9, the fracture surfaces of the axial connecting portions are wrapped by loose and soft corrosion products. The wave-shaped annular structures remain intact in the fourth month and play a role in radial support in the early stage. Then, the wave-shaped annular structures begin to corrode rapidly. The wave-shaped annular structures are radially deconstructed in the sixth month. It can be seen from FIG. 10 that the fracture surfaces of the wave-shaped annular structures are wrapped by the loose and soft corrosion products.

The area stenosis rate measured by OCT in the first month is 18%, the area stenosis rate measured by the OCT in the sixth month is 29%, and the area stenosis rate measured by the OCT in the twelfth month is 36%.

EXAMPLE 2

An absorbable metal stent is an absorbable coronary stent, which includes an absorbable metal substrate. The material of the absorbable metal substrate is nitrided iron. The stent has a wall thickness of 50 μm. The absorbable metal substrate includes 15 wave-shaped annular structures which are connected through axial connecting portions and are axially arranged, where every two adjacent wave-shaped annular structures are connected by three axial connecting portions. Each axial connecting portion is an Ω connecting portion, and two free ends of the Ω connecting portion are respectively connected to two adjacent wave-shaped annular structures. Each wave-shaped annular structure includes 6 wave peaks, 6 wave troughs and 12 support rods. A first corrosion inhibition layer is provided on each of the wave-shaped annular structures to cover an outer surface, an inner surface and side surfaces of the wave-shaped annular structure. The material of the first corrosion inhibition layers is zinc. The thicknesses of the first corrosion inhibition layer at the wave peaks and wave troughs are 0.8 μm respectively, and the thickness of the first corrosion inhibition layer at each support rod is 1 μm. A second corrosion inhibition layer is provided on each axial connecting portion. The material of the second corrosion inhibition layers is zinc. Each second corrosion inhibition layer has a thickness of 0.8 μm. A corrosion-promoting coating is provided on each axial connecting portion to cover the surface of the second corrosion inhibition layer, and the material of the corrosion-promoting coatings is polylactic acid. A degradable polymer layer is also provided on each wave-shaped annular structure. Each degradable polymer layer covers the surface of the first corrosion inhibition layer, and the material of the degradable polymer layer is also polylactic acid. Both the corrosion-promoting coatings and the degradable polymer layers contain rapamycin. Each corrosion-resistant coating has a thickness of 20 μm, a molecular weight of 200,000, and a polydispersity coefficient of 1.35. Each degradable polymer layer has a thickness of 12 μm, a molecular weight of 200,000, and a polydispersity coefficient of 1.35.

The absorbable coronary stent is implanted into the coronary artery of a pig, and the over-expansion ratio is maintained during the implantation process from 1.1:1 to 1.2:1. The absorbable coronary stent is kept intact in the third month. In the fourth month, the axial connecting portions, the absorbable coronary stent is axially deconstructed, and there are a lot of corrosion products at the fracture surfaces. In the sixth month, the wave peaks and/or wave troughs of the wave-shaped annular structures fracture, the absorbable coronary stent is radially deconstructed, and the fracture surfaces of the wave-shaped annular structures are wrapped by loose and softer corrosion products.

The area stenosis rate measured by OCT in the first month is 17%, the area stenosis rate measured by the OCT in the fourth month is 25%, and the area stenosis rate measured by the OCT in the twelfth month is 35%.

EXAMPLE 3

The structure of the absorbable metal stent in Example 3 is basically the same as that of Example 2, except that the thicknesses of each first corrosion inhibition layer at the wave peaks and wave troughs are both 1.5 μm, and the thickness of the first corrosion inhibition layer at each support rod is 2.0 μm. The second corrosion inhibition layer has a thickness of 1.5 μm. The materials of the corrosion-promoting coatings and the degradable polymer layers are both polyglycolic acid. Each corrosion-resistant coating has a thickness of 25 μm, a molecular weight of 500,000, and a polydispersity coefficient of 10. The degradable polymer layer has a thickness of 16 μm, a molecular weight of 1,000,000, and a polydispersity coefficient of 10. Both the corrosion-promoting coatings and the degradable polymer layers contain rapamycin.

The absorbable coronary stent is implanted into the coronary artery of a pig, and the over-expansion ratio is maintained during the implantation process from 1.1:1 to 1.2:1. The absorbable coronary stent is kept intact in the third month. The stent remains intact in the sixth month. In the seventh month, the axial connecting portions fracture, the absorbable coronary stent is axially deconstructed, and there are a lot of corrosion products at the fracture surfaces. In the ninth month, the wave peaks and/or wave troughs of the wave-shaped annular structures fracture, the absorbable coronary stent is radially deconstructed, and the fracture surfaces of the wave-shaped annular structures are wrapped by loose and softer corrosion products.

The area stenosis rate measured by OCT in the first month is 15%, the area stenosis rate measured by the OCT in the ninth month is 26%, and the area stenosis rate measured by the OCT in the twelfth month is 36%.

EXAMPLE 4

The structure of the absorbable metal stent in Example 4 is basically the same as that of the absorbable metal stent in Example 2, except that the thicknesses of each first corrosion inhibition layer at the wave peaks and wave troughs are both 0.4 μm, and the thickness of the first corrosion inhibition at each support rod is 0.8 m. The second corrosion inhibition layer has a thickness of 0.4 μm. The materials of the corrosion-promoting coatings and the degradable polymer layers are both polyitaconic anhydride. Each corrosion-resistant coating has a thickness of 20 μm, a molecular weight of 50,000, and a polydispersity coefficient of 1.2. The thicknesses of each degradable polymer layer at the wave peaks and wave troughs are both 12 μm. Each degradable polymer layer has a thickness of 10 μm at the support rod, a molecular weight of 100,000, and a polydispersity coefficient of 1.1. Both the corrosion-promoting coatings and the degradable polymer layers contain paclitaxel.

The absorbable coronary stent is implanted into the coronary artery of a pig, and the over-expansion ratio is maintained during the implantation process from 1.1:1 to 1.2:1. In the second month, the axial connecting portions of the absorbable coronary stent fracture, the absorbable coronary stent is axially deconstructed, and there are a lot of corrosion products at the fracture surfaces. In the third month, the wave-shaped annular structures still remain intact and play a role in radial support in the early stage. In the fourth month, the wave peaks and/or wave troughs of the wave-shaped annular structures fracture, the absorbable coronary stent is radially deconstructed, and the fracture surfaces of the wave-shaped annular structures are wrapped by loose and softer corrosion products.

The area stenosis rate measured by OCT in the first month is 18%, the area stenosis rate measured by the OCT in the sixth month is 32%, and the area stenosis rate measured by the OCT in the twelfth month is 34%.

EXAMPLE 5

The structure of the absorbable metal stent in Example 5 is basically the same as that of the absorbable metal stent in Example 1, except that each first corrosion inhibition layer has a thickness of 0.4 μm and each second corrosion inhibition layer has a thickness of 0.4 μm. The materials of the corrosion-promoting coatings and the degradable polymer layers are both polycaprolactone. Each corrosion-promoting coating has a thickness of 6 μm, a molecular weight of 400,000, and a polydispersity coefficient of 5. The thickness of each degradable polymer layer is 5 μm. The molecular weights of polycaprolactone at the wave peaks and wave troughs are both 450,000. Each degradable polymer layer has a molecular weight of 500,000 at the support rod, and a polydispersity coefficient of 4. Both the corrosion-promoting coatings and the degradable polymer layers are free of a drug, respectively.

The absorbable coronary stent is implanted into the coronary artery of a pig, and the over-expansion ratio is maintained during the implantation process from 1.1:1 to 1.2:1. In the second month, the axial connecting portions of the absorbable coronary stent fracture, the absorbable coronary stent is axially deconstructed, and there are a lot of corrosion products at the fracture surfaces. The wave-shaped annular structures still remain intact in the third month and play a role in radial support in the early stage. In the fourth month, the wave peaks and/or wave troughs of the wave-shaped annular structures fracture, the absorbable coronary stent is radially deconstructed, and the fracture surfaces of the wave-shaped annular structures are wrapped by loose and softer corrosion products.

The area stenosis rate measured by OCT in the first month is 18%, the area stenosis rate measured by the OCT in the sixth month is 32%, and the area stenosis rate measured by the OCT in the twelfth month is 38%.

EXAMPLE 6

The structure of the absorbable metal stent in Example 6 is basically the same as that of the absorbable metal stent in Example 1, except that the materials of the corrosion-promoting coatings and the degradable polymer layers are both polylysine. Each corrosion-promoting coating has a thickness of 20 μm, a molecular weight of 200,000, and a polydispersity coefficient of 1.35. Each degradable polymer layer has a thickness of 12 μm, a molecular weight of 250,000, and a polydispersity coefficient of 1.3 at the wave peaks and wave troughs. The polymer at the support rods has a polydispersity coefficient of 1.1. Both the corrosion-promoting coatings and the degradable polymer layers contain cilostazol.

The absorbable coronary stent is implanted into the coronary artery of a pig, and the over-expansion ratio is maintained during the implantation process from 1.1:1 to 1.2:1. The absorbable coronary stent remains intact in the third month. In the fourth month, the axial connecting portions of the stent fracture, the absorbable coronary stent is axially deconstructed, there are a lot of corrosion products at the fracture surfaces, and the wave-shaped annular structures remain intact. In the sixth month, the wave peaks and/or wave troughs of the wave-shaped annular structures fracture, the absorbable coronary stent is radially deconstructed, and the fracture surfaces of the wave-shaped annular structures are wrapped by loose and softer corrosion products.

The area stenosis rate measured by OCT in the first month is 18%, the area stenosis rate measured by the OCT in the sixth month is 28%, and the area stenosis rate measured by the OCT in the twelfth month is 35%.

EXAMPLE 7

The structure of the absorbable metal stent in Example 7 is basically the same as that of the absorbable metal stent in Example 6, except that the material of the wave-shaped annular structures is nitrided iron, the material of the axial connecting portions is a magnesium alloy, a second corrosion inhibition layer is absent, and each first corrosion inhibitor layer has a thickness of 1 μm. The materials of the corrosion-promoting coatings and the degradable polymer layers are both polylactic acid. Each corrosion-promoting coating has a thickness of 15 μm, a molecular weight of 200,000, and a polydispersity coefficient of 1.35. Each absorbable polymer has a thickness of 12 μm, a molecular weight of 200,000, a polydispersity coefficient of 1.3 at wave peaks and wave troughs, and a polydispersity coefficient of 1.1 at the support rod. Both the corrosion-promoting coatings and the degradable polymer layers contain rapamycin.

The absorbable coronary stent is implanted into the coronary artery of a pig, and the over-expansion ratio is maintained during the implantation process from 1.1:1 to 1.2:1. In the first month, the axial connecting portions of the stent fracture, the absorbable coronary stent is axially deconstructed, there are a lot of corrosion products at the fracture surfaces, and the wave-shaped annular structures of the stent remain intact. The stent remains axially intact in the third month. In the fourth month, the wave peaks and/or wave troughs of the wave-shaped annular structures fracture, the absorbable coronary stent is radially deconstructed, and the fracture surfaces of the wave-shaped annular structures are wrapped by loose and softer corrosion products.

The area stenosis rate measured by OCT in the first month is 20%, the area stenosis rate measured by the OCT in the fourth month is 25%, and the area stenosis rate measured by the OCT in the twelfth month is 36%.

EXAMPLE 8

The structure of the absorbable metal stent in Example 8 is basically the same as that of the absorbable metal stent Example 1, except that the material of the absorbable metal substrate is a magnesium alloy. The stent has a wall thickness of 70 μm. The materials of the first and second corrosion inhibition layers are both sodium silicate. Each first corrosion inhibition layer has a thickness of 2 μm. Each second corrosion inhibition layer has a thickness of 1 μm. The materials of the corrosion-promoting coatings and the degradable polymer layers are both polylactic acid. Each corrosion-promoting coating has a thickness of 15 μm, a molecular weight of 200,000, and a polydispersity coefficient of 1.35. Each degradable polymer layer has a thickness of 10 μm, a molecular weight of 200,000, and a polydispersity coefficient of 1.35. Both the corrosion-promoting coatings and the degradable polymer layers contain rapamycin.

The absorbable coronary stent is implanted into the coronary artery of a pig, and the over-expansion ratio is maintained during the implantation process from 1.1:1 to 1.2:1. In the third month, the axial connecting portions of the stent fracture, the absorbable coronary stent is axially deconstructed, there are a lot of corrosion products at the fracture surfaces, and the wave-shaped annular structures remain intact. In the fourth month, the wave-shaped annular structures fracture, the absorbable coronary stent is radially deconstructed, and the fracture surfaces of the wave-shaped annular structures are wrapped by loose and softer corrosion products.

The area stenosis rate measured by OCT in the first month is 18%, the area stenosis rate measured by the OCT in the fourth month is 26%, and the area stenosis rate measured by the OCT in the twelfth month is 36%.

EXAMPLE 9

The structure of the absorbable metal stent in Example 9 is basically the same as that of the absorbable metal stent in Example 1, except that each first corrosion inhibition layer has a thickness of 0.8 μm and each second corrosion inhibition layer has a thickness of 0.5 μm. The corrosion-promoting coatings and the degradable polymer layers are both polysuccinate. Each of the corrosion-promoting coating and the degradable polymer layer has a thickness of 12 μm, a molecular weight of 250,000, and a polydispersity coefficient of 2. Each degradable polymer layers contains cilostazol. The corrosion-promoting coatings are free of a drug.

The absorbable coronary stent is implanted into the coronary artery of a pig, and the over-expansion ratio is maintained during the implantation process from 1.1:1 to 1.2:1. In the third month, the axial connecting portions of the stent fracture, the absorbable coronary stent is axially deconstructed, there are a lot of corrosion products at the fracture surfaces, and the wave-shaped annular structures remain intact. In the sixth month, the wave-shaped annular structures are radially deconstructed, and the fracture surfaces of the wave-shaped annular structures are wrapped by loose and softer corrosion products.

The area stenosis rate measured by OCT in the first month is 19%, the area stenosis rate measured by the OCT in the sixth month is 30%, and the area stenosis rate measured by the OCT in the twelfth month is 35%.

EXAMPLE 10

The structure of the absorbable metal stent in Example 10 is basically the same as that of the absorbable metal stent in Example 1, except that each corrosion-promoting coating in Example 10 further contains polyproanthocyanidin, that is, the material of the corrosion-promoting coatings is formed by spraying after mixing polylactic acid and polyproanthocyanidin, where a mass ratio of polyproanthocyanidin to polylactic acid is 1:5. Each corrosion-promoting coating has a thickness of 15 μm, a molecular weight of polylactic acid of 100,000, a molecular weight of polyproanthocyanidin of 1,000, and a polydispersity coefficient of 1.35. Each degradable polymer layer has a thickness of 12 μm, a molecular weight of 200,000, and a polydispersity coefficient of 1.35. The coating is free of a drug.

The absorbable coronary stent is implanted into the coronary artery of a pig, and the over-expansion ratio is maintained during the implantation process from 1.1:1 to 1.2:1. The stent remains intact in the third month. In the fourth month, the axial connecting portions fracture, and the absorbable coronary stent is axially deconstructed. As can be seen from Micro-CT, the fracture surfaces of the axial connecting portions are wrapped by loose and soft corrosion products. The wave-shaped annular structures remain intact in the fourth month and play a role in radial support in the early stage. Then, the wave-shaped annular structures begin to corrode rapidly. In the sixth month, the wave-shaped annular structures are radially deconstructed, and the fracture surfaces of the wave-shaped annular structures are wrapped by loose and softer corrosion products.

The area stenosis rate measured by OCT in the first month is 18%, the area stenosis rate measured by the OCT in the sixth month is 29%, and the area stenosis rate measured by the OCT in the twelfth month is 36%.

EXAMPLE 11

The structure of the absorbable metal stent in Example 11 is basically the same as that of the absorbable stent in Example 1, except that the material for the corrosion-promoting coatings is an ascorbic acid and polycaprolactone copolymer. The coating is free of a drug. Each corrosion-promoting coating has a thickness of 20 μm, a molecular weight of 200,000, and a polydispersity coefficient of 1.35. Each degradable polymer layer has a thickness of 12 μm, a molecular weight of 200,000, and a polydispersity coefficient of 1.35. The coating is free of a drug.

The absorbable coronary stent is implanted into the coronary artery of a pig, and the over-expansion ratio is maintained during the implantation process from 1.1:1 to 1.2:1. The stent remains intact in the third month. In the fourth month, the axial connecting portions fracture, and the absorbable coronary stent is axially deconstructed. As can be seen from Micro-CT, the fracture surfaces of the axial connecting portions are wrapped by loose and soft corrosion products. The wave-shaped annular structures remain intact in the fourth month and play a role in radial support in the early stage. Then, the wave-shaped annular structures begin to corrode rapidly. In the sixth month, the wave-shaped annular structures are radially deconstructed, and the fracture surfaces of the wave-shaped annular structures are wrapped by the loose and soft corrosion products. The area stenosis rate measured by OCT in the first month is 18%, the area stenosis rate measured by the OCT in the sixth month is 30%, and the area stenosis rate measured by the OCT in the twelfth month is 35%.

EXAMPLE 12

The structure of the absorbable metal stent in Example 12 is basically the same as that of the absorbable metal stent in Example 1, except that the absorbable metal stent in Example 12 does not contain first corrosion inhibition layers, second corrosion inhibition layers and degradable polymer layers. The material of the corrosion-promoting coatings is polylactic acid. Each corrosion-promoting coating has a thickness of 12 μm, a molecular weight of 200,000, and a polydispersity coefficient of 1.35.

The absorbable coronary stent is implanted into the coronary artery of a pig, and the over-expansion ratio is maintained during the implantation process from 1.1:1 to 1.2:1. In the first month, the axial connecting portions of the stent fracture, the absorbable coronary stent is axially deconstructed, the fracture surfaces are wrapped by the loose and soft corrosion products, and the stent remains intact axially. In the third month, the wave-shaped annular structures begin to be deconstructed radially.

The area stenosis rate measured by OCT in the first month is 19%, the area stenosis rate measured by the OCT in the sixth month is 28%, and the area stenosis rate measured by the OCT in the twelfth month is 38%.

EXAMPLE 13

The structure of the absorbable metal stent in Example 13 is basically the same as that of the absorbable metal stent in Example 1, except that the thicknesses of the first corrosion inhibition layers and the second corrosion inhibition layers of the absorbable metal stent in Example 13 are both 0.5 μm. There is no degradable polymer layer. The material of the corrosion-promoting coatings is polylactic acid. Each corrosion-promoting coating has a thickness of 12 μm, a molecular weight of 200,000, and a polydispersity coefficient of 1.35.

The absorbable coronary stent is implanted into the coronary artery of a pig, and the over-expansion ratio is maintained during the implantation process from 1.1:1 to 1.2:1. In the third month, the axial connecting portions of the stent fracture, the absorbable coronary stent is axially deconstructed, the fracture surfaces are wrapped by the loose and soft corrosion products, and the stent remains intact radially. The wave-shaped annular structures begin to be deconstructed radially in the sixth month.

The area stenosis rate measured by OCT in the first month is 18%, the area stenosis rate measured by the OCT in the sixth month is 26%, and the area stenosis rate measured by the OCT in the twelfth month is 35%.

COMPARATIVE EXAMPLE 1

Figure 11:
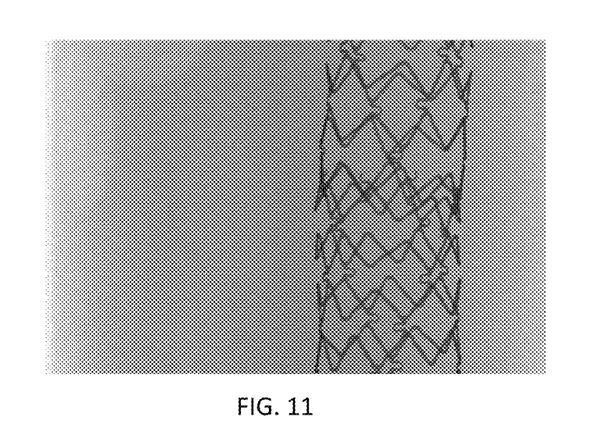
FIG. 11 is a Micro-CT picture of an absorbable coronary stent in Comparative Example 1 after 3 months of implantation.

The structure of the absorbable metal stent in Comparative Example 1 is basically the same as that of the absorbable metal stent in Example 1, except that each of the corrosion-promoting coating and the degradable polymer layer has a thickness of 3 μm, a molecular weight of 30,000, and a polydispersity coefficient of 1.35. The absorbable coronary stent is implanted into the coronary artery of a pig, and the over-expansion ratio is maintained during the implantation process from 1.1:1 to 1.2:1. The stent remains intact in the second month. In the third month, as shown in FIG. 11, a circle of axial connecting portions of the absorbable metal stent fracture with one wave circle in front of the fracture surface or one wave circle at the rear of the fracture surface being overlapped together, without obvious corrosion products.

The stenosis rate measured by the OCT in the first month is 25%, and the area stenosis rate measured by the OCT in the sixth month is 55%.

It can be seen that, compared with Comparative Example 1, the stenosis rates in the Examples 1 to 13 are reduced significantly.

The features of the above-described examples may be combined, as desired. For the sake of brevity of description, all possible combinations of the features in the above examples are not described. However, as long as there is no contradiction between the combinations of these features, they should be considered as the scope of the description.

The above-described examples are merely illustrative of several embodiments of the present embodiments, and the description thereof is more specific and detailed, but is not to be construed as limiting the scope of the present embodiments. It should be noted that a number of variations and modifications may be made by those of ordinary skill in the art without departing from the concept of the present embodiments, and all fall within the protection scope of the present embodiments.

The invention claimed is:

1. An absorbable metal stent, comprising an absorbable metal substrate, wherein the absorbable metal substrate comprises a plurality of wave-shaped annular structures and a plurality of axial connecting portions, two ends of each axial connecting portion being connected to two adjacent wave-shaped annular structures respectively so as to axially connect the plurality of wave-shaped annular structures; a corrosion-promoting coating is formed on each axial connecting portion, the corrosion-promoting coating containing a corrosion-promoting substance, and the corrosion-promoting substance being selected from at least one of a degradable polymer and a degradable polymer antioxidant; and the corrosion-promoting coatings make the corrosion of the axial connecting portions to occur earlier than the corrosion of the plurality of wave-shaped annular structures; wherein the absorbable metal stent further comprises a first corrosion inhibition layer, and the first corrosion inhibition layer is formed on each of the wave-shaped annular structures;

wherein the absorbable metal stent is configured to preferentially be axially deconstructed in sequence after implantation of the absorbable metal stent to form a plurality of independent wave-shaped annular structures;

wherein the absorbable metal stent further comprises a degradable polymer layer provided on each of the wave-shaped annular structures, and wherein the degradable polymer in the degradable polymer layers and the corrosion-promoting substance in the corrosion-promoting coatings are formed from the same structural units, and a polydispersity coefficient of the corrosion-promoting substance in the corrosion-promoting coatings is greater than a polydispersity coefficient of the degradable polymer in the degradable polymer layers.

2. The absorbable metal stent according to claim 1, wherein the degradable polymer is selected from at least one of a degradable polyester, a degradable polyanhydride, and a degradable polyamino acid; and a chain segment or monomer released when the degradable polymer antioxidant is degraded includes at least one of ascorbic acid, glutathione, lipoic acid, and proanthocyanidin.

3. The absorbable metal stent according to claim 1, wherein a second corrosion inhibition layer is formed on each of the axial connecting portions, the corrosion-promoting coating at least partially covers the second corrosion inhibition layer, and the thickness of the first corrosion inhibition layer is greater than or equal to the thickness of the second corrosion inhibition layer.

4. The absorbable metal stent according to claim 1, wherein each of the wave-shaped annular structures comprises a plurality of wave peaks, a plurality of wave troughs, and a plurality of support rods; two ends of each of the support rods are respectively connected to one of the wave peaks and one of the wave troughs, which are adjacent to each other, to form the wave-shaped annular structure; each first corrosion inhibition layer is a coating having a non-uniform thickness, and the thicknesses of portions of the first corrosion inhibition layer located at the wave peak and the wave trough are less than or equal to the thickness of the first corrosion inhibition layer located at the support rod, respectively.

5. The absorbable metal stent according to claim 1, wherein the absorbable metal substrate is an iron substrate, an iron-based alloy substrate, a magnesium substrate, a magnesium-based alloy substrate, a zinc substrate or a zinc-based alloy substrate.

6. The absorbable metal stent according to claim 1, wherein the wave-shaped annular structures are made of iron or an iron-based alloy, and the axial connecting portions are made of a magnesium alloy.

7. The absorbable metal stent according to claim 2, wherein the material of the degradable polymer layer is selected from at least one of a degradable polyester, a degradable polyanhydride, and a degradable polyamino acid.

8. The absorbable metal stent according to claim 7, wherein the thickness of each degradable polymer layer is less than or equal to the thickness of each corrosion-promoting coating.

9. The absorbable metal stent according to claim 7, wherein a molecular weight of the degradable polymer in the corrosion-promoting coatings is less than or equal to a molecular weight of the degradable polymer in the degradable polymer layers.

10. The absorbable metal stent according to claim 7, wherein each of the wave-shaped annular structures comprises a plurality of wave peaks, a plurality of wave troughs, and a plurality of support rods; two ends of each of the support rods are respectively connected to one of the wave peaks and one of the wave troughs, which are adjacent to each other, to form the wave-shaped annular structure; the degradable polymer layer is a coating having a non-uniform thickness, and the thicknesses of portions of the degradable polymer layer located at the wave peak and the wave trough are greater than or equal to the thickness of the degradable polymer layer located at the support rod, respectively.

11. The absorbable metal stent according to claim 7, wherein each of the wave-shaped annular structures comprises a plurality of wave peaks, a plurality of wave troughs, and a plurality of support rods; two ends of each of the support rods are respectively connected to one of the wave peaks and one of the wave troughs, which are adjacent to each other, to form the wave-shaped annular structure; and a molecular weight of the degradable polymer in portions of the degradable polymer layer located at the wave peak and the wave trough is less than or equal to a molecular weight of the degradable polymer in the degradable polymer layer located at the support rod.

12. The absorbable metal stent according to claim 7, wherein each of the wave-shaped annular structures comprises a plurality of wave peaks, a plurality of wave troughs, and a plurality of support rods; two ends of each of the support rods are respectively connected to one of the wave peaks and one of the wave troughs, which are adjacent to each other, to form the wave-shaped annular structure; and polydispersity coefficients of the degradable polymer in portions of the degradable polymer layer located at the wave peak and the wave trough are greater than or equal to a polydispersity coefficient of the degradable polymer in the degradable polymer layer located at the support rod.

13. The absorbable metal stent according to claim 2, wherein the degradable polyester is selected from at least one of the group consisting of polylactic acid, polyglycolic acid, polycaprolactone, polysuccinate, poly(β-hydroxybutyrate), polyethyl dialcohol adipate, and polyhydroxybutyrate valerate, or the degradable polyester is selected from a copolymer formed by copolymerizing at least two kinds of monomers forming polylactic acid, polyglycolic acid, polycaprolactone, polysuccinate, poly(β-hydroxybutyrate), polyethyl dialcohol adipate, and polyhydroxybutyrate valerate.

14. The absorbable metal stent according to claim 2, wherein the degradable polyanhydride is selected from at least one of the group consisting of polyoxalic anhydride, polybutanedioic anhydride, polyadipic anhydride, polysebacic anhydride, polydodecanoic anhydride, polycitric anhydride, polymalic anhydride, polysuccinic anhydride, polytartaric anhydride, polyitaconic anhydride, and polymaleic anhydride; or the degradable polyanhydride is a copolymer formed by copolymerizing at least one of monomers forming polyoxalic anhydride, polybutanedioic anhydride, polyadipic anhydride, polysebacic anhydride, polydodecanoic anhydride, polycitric anhydride, polymalic anhydride, polysuccinic anhydride, polytartaric anhydride, polyitaconic anhydride and polymaleic anhydride, and at least one of monomers forming polylactic acid, polyglycolic acid, polycaprolactone, polysuccinate, poly(β-hydroxybutyrate), polyethyl dialcohol adipate, and polyhydroxybutyrate valerate.

15. The absorbable metal stent according to claim 2, wherein the monomer that forms the degradable polyamino acid is selected from at least one of monomers forming polylysine, polyaspartic acid, polycysteine, polymethionine, polyornithine, polyglycine, and polyglutamic acid.

16. The absorbable metal stent according to claim 7, wherein the anti-corrosion coating and/or the degradable polymer layer contains an active drug, the active drug being selected from at least one of the group consisting of a drug that inhibits vascular proliferation, an antiplatelet drug, an antithrombotic drug, an anti-inflammatory drug and an anti-allergenic drug.

17. The absorbable metal stent according to claim 16, wherein the drug that inhibits vascular proliferation is selected from at least one of paclitaxel, rapamycin and derivatives thereof; the anti-platelet drug is cilostazol; the antithrombotic drug is heparin; the anti-inflammatory drug is dexamethasone; and the anti-allergenic drug is selected from at least one of calcium gluconate, chlorpheniramine and cortisone.

18. The absorbable metal stent according to claim 1, wherein the first corrosion inhibition layer is only formed on each of the wave shaped annular structures.

19. The absorbable metal stent according to claim 1, wherein the corrosion-promoting coating is only formed on each axial connecting portion.

* * * * *